US006756506B2

(12) United States Patent
Kroker et al.

(10) Patent No.: US 6,756,506 B2
(45) Date of Patent: Jun. 29, 2004

(54) METHOD FOR PRODUCING TERT-BUTYL ESTERS OF ALIPHATIC C1-C4-CARBOXYLIC ACIDS

(75) Inventors: Ruprecht Kroker, Bobenheim-Roxheim (DE); Gerhard Nestler, Ludwigshafen (DE); Werner Schmitt, Frankenthal (DE); Winfried Schumm, Gelsenkirchen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/334,000

(22) PCT Filed: Jul. 27, 2001

(86) PCT No.: PCT/EP01/08710

§ 371 (c)(1),
(2), (4) Date: Jan. 27, 2003

(87) PCT Pub. No.: WO02/10109

PCT Pub. Date: Feb. 7, 2002

(65) Prior Publication Data

US 2003/0181754 A1 Sep. 25, 2003

(30) Foreign Application Priority Data

Jul. 28, 2000 (DE) .......................................... 100 36 959

(51) Int. Cl.$^7$ ........................... C07C 69/02; C07C 67/38
(52) U.S. Cl. ........................................ 560/233; 560/231
(58) Field of Search ................................ 560/129, 205, 560/231, 233

(56) References Cited

U.S. PATENT DOCUMENTS 3,031,495 A 4/1962 Young et al.
3,037,052 A 5/1962 Bortnick
3,082,246 A 3/1963 Chafetz
3,087,962 A 4/1963 Bortnick
3,088,969 A 5/1963 Callahan et al.
3,172,905 A 3/1965 Eckert

FOREIGN PATENT DOCUMENTS

| DE | 11 28 428 | 4/1962 |
| DE | 11 35 897 | 9/1962 |
| DE | 31 05 399 | 10/1982 |
| EP | 0 268 999 | 6/1988 |
| GB | 934 917 | 8/1963 |

OTHER PUBLICATIONS

"Methoden der organischen chemie" HOUBEN–WEYL, vol. 8, p. 534 1952.

Primary Examiner—Johann Richter
Assistant Examiner—Karl Puttlitz
(74) Attorney, Agent, or Firm—Oblon, Spivak, McClelland, Maier & Neustadt, P.C.

(57) ABSTRACT

The tert-butyl ester of an aliphatic $C_1$–$C_4$-carboxylic acid is prepared by reacting the carboxylic acid with isobutene in the liquid phase in the presence of an acidic catalyst by a continuous process in which the reaction is carried out in a reactor divided into a plurality of sections, the carboxylic acid, the isoolefin and the catalyst are fed into the first section of the reactor, the reaction mixture obtained is removed from the last section of the reactor and the ester is isolated therefrom, the reaction temperature in the reactor being controlled so that it is from 10 to 40° C. and is highest in the first section of the reactor.

The novel process permits the technically simple, economical and environmentally friendly preparation of tertiary butyl esters of saturated and unsaturated $C_1$–$C_4$-carboxylic acids.

10 Claims, 1 Drawing Sheet

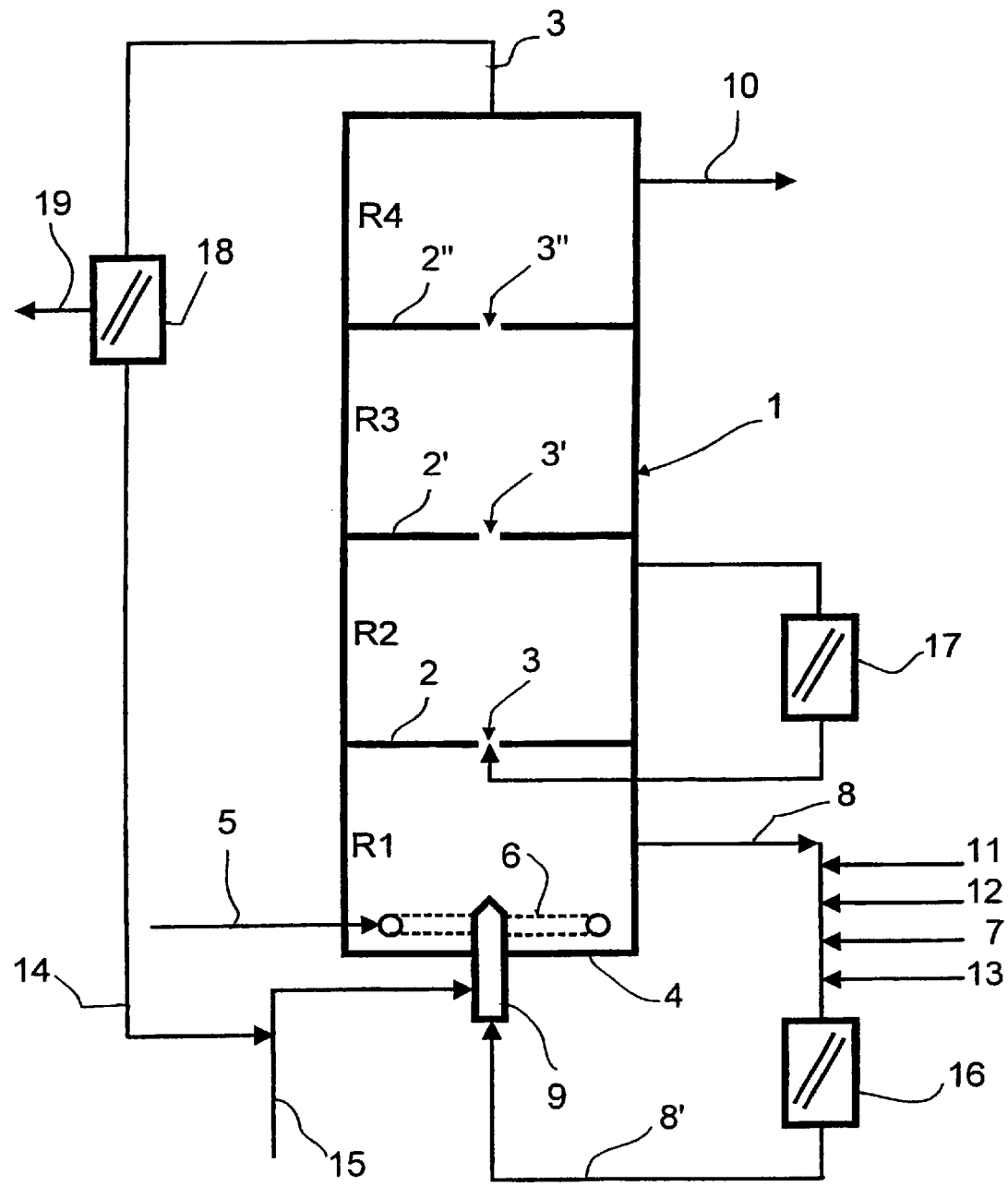

METHOD FOR PRODUCING TERT-BUTYL ESTERS OF ALIPHATIC C1-C4-CARBOXYLIC ACIDS

The present invention relates to a continuous process for the preparation of the tert-butyl ester of an aliphatic $C_1$–$C_4$-carboxylic acid by reacting the carboxylic acid with isobutene.

The novel process leads to tert-butyl esters of aliphatic $C_1$–$C_4$-carboxylic acids. Such esters are widely used. The tert-butyl esters of saturated aliphatic carboxylic acids, such as tert-butyl acetate, are used, for example, as solvents. tert-Butyl esters of (meth)acrylic acid are important starting materials for the preparation of polymers which are used, inter alia, as components of coating dispersions, adhesives or coating resins. tert-Butyl esters are generally prepared by an acid-catalyzed addition reaction of the corresponding carboxylic acids with isobutene (Houben-Weyl, Methoden der Organischen Chemie, Vol. 8, 1952, page 534; U.S. Pat. No. 3,031,495 and U.S. Pat. No. 3,082,246). The catalysts used are acids which are soluble in the reaction mixture, for example mineral acids or alkanesulfonic or arylsulfonic acids (DE-A-12 49 857, U.S. Pat. No. 3,087,962, U.S. Pat. No. 3,088,969), or insoluble catalysts, such as acidic ion-exchange resins (U.S. Pat. No. 3,037,052, U.S. Pat. No. 3,031,495, DE-A-31 05 399, EP-A-268 999).

The reaction of the carboxylic acids with isobutene is carried out as a rule in conventional reaction containers or in columns (DE-A-11 28 428), the thorough mixing of the reaction mixture being effected by stirring or by means of the isobutene stream passed in. The heat is removed in a conventional manner.

The reaction mixture obtained is first freed from the catalyst. With the use of a catalyst soluble in the reaction mixture, this is generally effected by washing with water and/or neutralization with an aqueous alkali solution (DE-A-11 28 428) or by distillation (DE-A-12 49 857). The reaction mixture freed from the catalyst is then worked up by distillation.

As a rule, the following difficulties occur in the preparation of tert-butyl esters:

oligomerization of the isobutene where $\alpha,\beta$-ethylenically unsaturated carboxylic acids are used, polymerization of the carboxylic acids or of the esters under thermal stress cleavage of the tert-butyl esters under the action of heat and/or in the presence of traces of strong acids insufficient removal of the heat of reaction occurring in the highly exothermic esterification reaction which may result in cleavage of the ester, oligomerization of the isobutene and, with the use of an $\alpha,\beta$-ethylenically unsaturated carboxylic acid, polymerization of the carboxylic acid and of the ester obtained. The last-mentioned effect leads to soiling of the apparatuses, blockage of pipes and pumps and coating of column trays and heat exchanger surfaces, which results in uneconomical and environmentally polluting cleaning of the plants.

In the prior art, numerous attempts have been made to reduce or to avoid the resulting difficulties. Thus, the tendency of isobutene to oligomerize can be reduced by lowering the reaction temperature (U.S. Pat. No. 3,172,905), by the presence of water (U.S. Pat. No. 3,088,969) and by partial neutralization of the catalyst (DE-A 31 05 399). However, these measures have the disadvantage that the reaction rate is reduced.

The formation of isobutene oligomers can also be reduced by using gaseous isobutene (DE-A-11 35 897). However, the disadvantage here is the necessary vaporization of the liquid isoolefins and the handling of large amounts of gas.

In order to avoid or reduce the polymerization of $\alpha,\beta$-ethylenically unsaturated compounds, in particular of (meth) acrylic compounds, polymerization inhibitors, such as phenothiazine, hydroquinone or tert-butylpyrocatechol or mixtures thereof, are frequently added, if required with simultaneous addition of air. However, the polymer formation cannot be completely prevented thereby.

In spite of all efforts however, there is no known process to date which reduces the abovementioned difficulties at least to such an extent that an advantageous industrial process results therefrom.

It is an object of the present invention to provide a technically simple, economical and environmentally friendly process for the preparation of tert-butyl esters of aliphatic carboxylic acids.

We have found, surprisingly, that this object is achieved if the reaction of the carboxylic acids with isobutene is carried out in a reactor having a plurality of sections and the reaction temperature in each section is controlled in such a way that it is from 10 to 40° C. in the reactor and is advantageously highest in the first section.

The present invention therefore relates to a process for the preparation of the tert-butyl ester of an aliphatic $C_1$–$C_4$-carboxylic acid by reacting the carboxylic acid with isobutene in the liquid phase in the presence of an acidic catalyst and isolating the ester from the reaction mixture obtained, wherein the reaction is carried out in a reactor divided into a plurality of sections and the carboxylic acid, the isobutene and the catalyst are fed into the first zone of the reactor, the reaction temperature in the reactor being controlled so that it is from 10 to 40° C. and is highest in the first section.

The aliphatic $C_1$–$C_4$-carboxylic acids are in particular formic acid, acetic acid, propionic acid, butyric acid, isobutyric acid, acrylic acid or methacrylic acid, acrylic acid or methacrylic acid being particularly preferred.

The isobutene is fed, preferably in liquid form, into the first section of the reactor. The ratio of carboxylic acid to isobutene may vary within a wide range. Preferably, however, the carboxylic acid is used in a molar excess. The molar ratio of carboxylic acid to isobutene is preferably from 1.1:1 to 1.5:1.

The process is carried out in general in the absence of a solvent. The catalysts used are therefore those which are at least partially soluble in the reaction mixture. In particular, the inorganic catalysts are only partially soluble in the reaction mixture at the beginning of the reaction. Such catalysts are therefore partially finely dispersed in the reaction mixture especially in the first and second sections. In the course of the reaction, the catalyst becomes more soluble (primarily owing to the formation of a partial ester of the catalyst, for example of the sulfuric acid monoester). At least in the last section, it is therefore generally present in dissolved form in the reaction mixture. Catalysts which may be used are strongly inorganic or organic acids, such as mineral acids, for example sulfuric acid, phosphoric acid and polyphosphoric acid, preferably sulfuric acid, or sulfonic acids, such as p-toluenesulfonic, benzenesulfonic, dodecylbenzenesulfonic and methanesulfonic acid.

The amount of catalyst is in general from about 0.1 to 10, preferably from 0.5 to 5, percent by weight, based on the starting materials carboxylic acid and isobutene.

The reaction is carried out in general also in the presence of an inhibitor which inhibits the polymerization of the unsaturated carboxylic acid or of the ester. Particularly suitable inhibitors are hydroquinone, hydroquinone monomethyl ether, p-benzoquinone, p-nitrosophenol, phenothiazine, 4-hydroxy-2,2,6,6-tetramethyl-1-oxylpiperidine and methylene blue. The inhibitors are used in general in amounts of from about 200 to 2000 ppm, based on the weight of the starting materials carboxylic acid and isoolefin.

The novel process is carried out in a reactor which may be in particular a cylindrical reactor. The reactor is divided into a plurality of sections, preferably 3, 4 or 5 sections, separated from one another. The sections are separated from one another by dividing walls which are perpendicular to the longitudinal axis of the reactor. Said dividing walls each have at least one orifice to permit the passage of the reaction mixture from one reactor section to the next. The number of orifices per dividing wall depends on the size of the reactor. Preferably, the dividing walls have one orifice which is present in particular in the center of the dividing wall. The total area of the orifices per dividing wall is from about $\frac{1}{2000}$ to $\frac{1}{500}$ of the cross-sectional area of the reactor.

The volume of the reactor sections may be identical or different. Preferably, the volume of the first reactor section is greater than that of the remaining sections. In a reactor having four sections, the following proportions of the individual sections, based on the total reactor volume, have proven preferable:

| reactor section 1 | from 25 to 50% |
| reactor section 2 | from 10 to 25% |
| reactor section 3 | from 10 to 25% |
| reactor section 4 | from 25 to 50% |

The reactor section can advantageously be equipped with internals in order to improve the mixing of the reaction mixture. Suitable internals are known to a person skilled in the art; for example, they may be static mixing elements, such as grilles, distributor plates or sieve trays. It is particularly preferable to equip the first reactor section with such internals, which in particular are provided in the upper half of the reactor section.

The starting materials carboxylic acid and isobutene are fed in liquid form into the first section, in particular in the region of the bottom of the reactor. Feeding may be effected directly, for example via a dip tube, but it is preferable to provide means which permit uniform distribution and thorough mixing of the starting materials. Such means are known to a person skilled in the art and are, for example, distributor plates, perforated plates and tubes, nozzles, etc. The isobutene is preferably fed in via an annular tube having a plurality of outlet orifices. The carboxylic acid is preferably fed in via a nozzle which effects mixing of a gas and of a liquid and thorough mixing of the reactor content. It is preferably arranged in the bottom of the reactor. Suitable nozzles are known to a person skilled in the art (jet nozzle, mixing nozzle, binary nozzle, etc.) and are described, for example, in Ullmann's Encyclopedia of Industrial Chemistry, Vol. B4, $5^{th}$ Edition, 1992, page 280. Particularly when such a nozzle is used, the flow in the first two reactor sections is turbulent and that in the following reactor sections is substantially laminar.

It has proven advantageous to feed the fresh carboxylic acid into the reactor in the form of a mixture with the residue from the catalyst removal and the residue from the purification redistillation (see below). Moreover, it has proven advantageous if isobutene obtained in the distillation of the ester is recycled to the first reactor section. When gaseous isobutene is used, it is particularly advantageous to feed in the isobutene via said nozzle together with the carboxylic acid. The nozzle ensures automatic aspiration of the recycled gasoues isobutene.

A part of the reaction mixture can be removed from the first and/or second reactor section and recycled to the relevant section. This ensures better mixing of the reaction mixture. The part-stream is expediently recycled via the abovementioned mixing nozzle into the first reactor section and/or via a further nozzle, in the region of the orifice present in the dividing wall, into the second reactor section. The further nozzle may be a nozzle of the type stated above for the mixing nozzle. A conical nozzle is preferably used. It is preferably arranged so that its outlet orifice is roughly at the height of the dividing wall which separates the first section from the second section. If desired, the part-stream removed in each case can be fed via a heat exchanger for controlling the temperature.

The reaction mixture obtained is removed at the upper end of the reactor and fed for further working-up. Unconverted, gaseous isobutene collects in the upper region of the reactor. It is recycled to the first reactor section, preferably via said nozzle at the bottom of the first reactor section. The isobutene-containing gas stream arriving from the reactor is preferably freed from inert gases, such as air and butane, by condensation of the isobutene. The isobutene is then fed in liquid form, via the mixing nozzle or together with the fresh isobutene, into the first reactor section.

The catalyst is fed in as a mixture with the carboxylic acid, it being possible to use fresh catalyst or recovered catalyst or a mixture thereof.

The reaction temperature is in general from about 10 to 40° C. It is preferably controlled so that it is highest in the first reactor section. Preferably, the reaction temperature in the first reactor section is from about 30 to 40° C. In the second section it is lower, preferably by from about 5 to 15° C. The temperature in the sections following the second section may be identical or different. It is generally not higher than that in the second section and is preferably lower, in particular by from about 3 to 10° C. In the fourth section, it is generally as high as in the third section or from about 1 to 5° C. lower. The temperature in the last reactor section is preferably from about 10 to 25° C.

The temperature distribution in a reactor having 4 sections is preferably as follows:

| $1^{st}$ section: | 33–38° C. |
| $2^{nd}$ section: | 23–28° C. |
| $3^{rd}$ section: | 15–22° C. |
| $4^{th}$ section: | 15–22° C. |

The temperature in the $3^{rd}$ and $4^{th}$ sections may be identical or different.

Since the addition reaction of carboxylic acids with isobutene is highly exothermic, it is expedient to remove the heat of reaction, at least in the first two reactor sections, in order to establish the reaction temperature. This is effected in particular with the aid of heat exchangers, which may be located externally or internally. Cooling of the reactor walls is also possible. It has proven expedient to control the temperature in the first two reactor sections with the aid of external heat exchangers, via which a part-stream of the reaction mixture present in the respective reactor section is passed and recycled.

The novel process can be carried out at superatmospheric, reduced or, preferably, atmospheric or slightly superatmospheric pressure (100–300 mbar).

The reaction mixture emerging from the reactor contains a high proportion of the desired ester. In addition, it contains unconverted starting materials, catalyst, inhibitor, esters of the catalyst acid and further small amounts of byproducts. The reaction mixture contains only very small amounts of isobutene oligomerization product, in general ≦2% by weight, based on the reaction mixture.

In order to isolate pure ester, the reaction mixture is subjected to a further working-up. The working-up is in no way restricted and can be effected by any process customary for this purpose. In an expedient procedure, the catalyst is first separated off. This can be carried out by washing the reaction mixture one or more times with water and/or by neutralizing the catalyst with an aqueous alkali solution (for example sodium hydroxide solution, potassium hydroxide solution or aqueous sodium or potassium carbonate or bicarbonate solution). Alternatively, the catalyst can be separated off by distilling the reaction mixture, for example in a distillation unit comprising evaporator, column and condenser. In this way, a top product which substantially comprises the desired ester, small amounts of carboxylic acid and low-boiling components (tert-butanol and diisoolefin) and a bottom product which comprises the catalyst, the main amount of the unconverted carboxylic acid and the high-boiling components, e.g. polymeric (meth) acrylic compounds, are obtained. The bottom product is generally recycled at least partly to the reactor.

The removal of the catalyst is followed by the removal of the low boilers in a conventional distillation unit comprising evaporator, column and condenser. The crude ester freed from the low boilers remains behind as bottom product and is then subjected to purification by distillation in a conventional manner. The residue of the purification by distillation, mainly carboxylic acid and a little ester, is recycled to the first reactor section.

The novel process has the following advantages:

simple and effective control of the reaction temperature, so that byproduct formation, in particular the formation of oligomerization products of isobutene, is extremely low;

the isobutene is used in liquid form, so that no energy-consumptive vaporization of the isobutene is required;

the reactor has a technically simple design, so that the capital costs are low;

owing to its simple design and the lack of moving parts, the reactor requires little maintenance, so that the operating costs are low;

recycled isobutene (exit gas from the working-up stages) can be reused in gaseous form, so that no liquefaction is required;

all carboxylic acid-containing residues can be recycled together;

the use of nozzles which are driven by the starting materials or the recycle streams results in good mixing of the reaction mixture;

the process permits problem-free recycling of the catalyst.

The novel process can be carried out not only with isobutene. It is advantageous with the use of an isoolefin of the formula

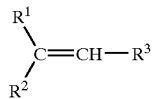

where $R^1$ and $R^2$, independently of one another, are methyl or ethyl and $R^3$ is H, methyl or ethyl. A tert-$C_4$–$C_8$-alkyl ester of an aliphatic $C_1$–$C_4$-carboxylic acid is obtained.

The novel process is explained below purely by way of example for the preparation of tert-butyl acrylate with reference to the figure and without restriction thereto.

The figure shows a schematic diagram of an axial longitudinal section through the novel reactor.

The reactor 1 having a total volume of about 10 m$^3$ (diameter about 1.3 m) is divided into four sections R1, R2, R3 and R4, which are separated from one another by dividing walls 2, 2', 2". In the center of each dividing wall is a round orifice 3, 3' or 3" (diameter up to about 5 cm) which permits the passage of the reaction mixture into the next chamber. The volumes of the reactor sections, based on the total volume, are: R1=about 40%, R2=about 15%, R3=about 15% and R4=about 30%. The first reactor section R1 is equipped in the upper half with a grille (not shown).

Fresh isobutene is fed in (500 l/h) via line 5 in the region of the bottom 4 of the reactor 1 or of the reactor section R1, in liquid form. The fresh isobutene is distributed by an annular tube 6 arranged symmetrically in the lower region of the reactor section R1 and having a plurality of outlet orifices (not shown). A mixture which consists of fresh acrylic acid 7 (430 l/h), the bottom product 11 from the catalyst removal (1150 l/h, acrylic acid content about 40% by weight), the bottom product 12 from the purification by distillation (320 l/h, acrylic acid content about 70% by weight), the fresh catalyst 13 (3.5 l/h, 98% strength sulfuric acid), the recycle isobutene 14 from the reactor exit gas, the discharge 8 from the reactor section R1 (about 75 m$^3$/h) and the gaseous recycle isobutene 15 (92 m$^3$/h) obtained in the distillations in the working-up of the resulting reaction mixture, is fed into the lower region of the reactor section R1 via the line 8 and the centrally arranged jet nozzle 9. The jet nozzle 9 aspirates the gaseous recycle isobutene 15 and the liquid recycle isobutene 14.

Thorough mixing of the starting materials is effected by the tube 6 and the nozzle 9. In order further to improve the mixing, a part of the reaction mixture is discharged in the upper region of the reactor section R1 and is recycled via the nozzle 9 into the reactor section R1. Said streams 7 and 11 to 13 are mixed into the discharged part-stream. The total stream 8' is passed via the heat exchanger 16 in order to remove the heat of reaction and to bring the temperature in the first reactor section to about 35° C.

The reaction mixture from the reactor R1 passes through the orifice 3 (diameter about 3 cm) into the reactor section R2. In the upper region of the reactor section R2, a part of the reaction mixture (4 m$^3$/h) is removed and is passed via the heat exchanger 17 to remove the heat of reaction and is recycled via a conical nozzle (not shown) to the reactor section R2. The nozzle is arranged in such a way that its outlet orifice is present in the orifice 3, roughly in the plane of the dividing wall 2. The reaction temperature in R2 is brought to about 25° C. in this way. As a result of the additional flow produced by said nozzle, the flow of the reaction mixture from R1 to R2 is supported and the content of R2 is thoroughly mixed. The transfer of the reaction mixture from R2 to R3 and from R3 to R4 takes place via the orifices 3' and 3", respectively (diameter in each case 2 cm). The heat removal in R3 and R4 is effected in each case via internal laminar coolers (not shown), the temperature being brought in each case to 20° C. The reaction mixture (2.4 m$^3$/h) is discharged from the reactor section R4 via a liquid level regulation means and via line 18 and is fed for further working-up.

The gas phase forming above the liquid phase in the reactor section R4 is removed at the top of the reactor and passed via a brine-operated condenser 18 in order to condense the isobutene contained in the exit gas and to separate said isobutene from the inert gases (2.5 m³/h, mainly butanes and air). The inert gases are disposed of via the line 19, and the liquid isobutene is recycled via the nozzle 9 to the reactor section R1.

The reactor discharge has substantially the following composition:

| | |
|---|---|
| tert-butyl acrylate | 64.0% by weight |
| tert-butyl acetate | 0.2% by weight |
| tert-butanol | 1.6% by weight |
| acrylic acid | 24.1% by weight |
| isobutene | 2.5% by weight |
| diisobutene | 1.2% by weight |
| sulfuric acid | 1.0% by weight |
| tert-butylsulfuric acid | 5.3% by weight |
| phenothiazine | 0.1% by weight |

For working-up, the reactor discharge is separated with the aid of a thin-film evaporator (80° C., 60 mbar) into a distillate which mainly contains tert-butyl acrylate, tert-butyl acetate, butanol and acrylic acid and a bottom product which substantially contains acrylic acid, catalyst and phenothiazine, and is recycled to the reactor. The distillate is mixed with 1000 ppm of phenothiazine and 500 ppm of p-nitrosophenol and is separated in a further conventional distillation column (40 trays, bottom temperature 78° C., top temperature 38° C. at 115 mbar) into a top product (low boilers), mainly tert-butyl acetate, diisobutene and tert-butanol, and a bottom product, mainly tert-butyl acrylate and acrylic acid. Some of the distillate is discharged (3% by volume) and some of it, mixed with 200 ppm of phenothiazine and 100 ppm of p-nitrosophenol, is recycled as reflux into the top of the column. In a further distillation column of known design (40 trays, bottom temperature 92° C., top temperature 49° C. at 75 mbar), the tert-butyl acrylate is obtained as top product, the bottom product, which contains about 70% by weight of acrylic acid, being recycled to the reactor. The isobutene-containing exit gases obtained in the distillation steps are combined and are recycled to the reactor. The condensed tert-butyl acrylate is stabilized with 15 ppm of hydroquinone monomethyl ether and some of it (about 50%) is fed as reflux to the uppermost tray of the column and some of it is discharged. The tert-butyl acrylate obtained in this manner has a purity of 99.9%.

We claim:

1. A process for the continuous preparation of the tert-butyl ester of an aliphatic $C_1$–$C_4$-carboxylic acid by reacting the carboxylic acid with isobutene in the liquid phase in the presence of an acidic catalyst, wherein the reaction is carried out in a reactor divided into a plurality of sections, the carboxylic acid, the isoolefin and the catalyst are fed into the first section of the reactor, the reaction mixture obtained is removed from the last section of the reactor and the ester is isolated therefrom, the reaction temperature in the reactor being controlled so that it is from 10 to 40° C. and is highest in the first section of the reactor.

2. A process as claimed in claim 1, wherein a reactor having from 3 to 5 sections is used.

3. A process as claimed in claim 1, wherein the reaction temperature in the first section is from 30 to 40° C.

4. A process as claimed in claim 1, wherein the reaction temperature in the second section is from 5 to 15° C. lower than that in the first section.

5. A process as claimed in claim 4, wherein the reaction temperature in the third section is from 3 to 10° C. lower than that in the second section.

6. A process as claimed in claim 1, wherein the reaction temperature in the first section of the reactor is from 30 to 40° C. and that in the last section of the reactor is from 10 to 25° C.

7. A process as claimed in claim 1, wherein a part of the reaction mixture contained in the first section is discharged and is recycled together with carboxylic acid to the first section.

8. A process as claimed in claim 1, wherein the isobutene fed into the first section comprises fresh and recycled isobutene, the fresh isobutene being fed in in liquid form and the recycled isobutene being fed in in liquid form and/or gaseous form.

9. A process as claimed in claim 8, wherein the recycled isobutene is fed in as a mixture with the carboxylic acid.

10. A process as claimed in claim 1, wherein the carboxylic acid used is (meth)acrylic acid or acetic acid.

* * * * *